United States Patent [19]
Daniele et al.

[11] Patent Number: 5,956,927
[45] Date of Patent: Sep. 28, 1999

[54] SUTURE CAPTURE AND TENSIONING ARRANGEMENT IN A MACHINE FOR THE AUTOMATED PACKAGING OF NEEDLES AND ATTACHED SUTURES

[75] Inventors: Robert A. Daniele, Flemington; Anthony Esteves, Somerville, both of N.J.; George Horst Reinemuth, Glen Mills; Richard Paul Branco, Collegeville, both of Pa.

[73] Assignee: Ethicon, Inc., Somerville, N.J.

[21] Appl. No.: 09/019,674

[22] Filed: Feb. 6, 1998

[51] Int. Cl.⁶ .................................................. B65B 63/04
[52] U.S. Cl. .................................. 53/430; 53/116; 53/118
[58] Field of Search ................................ 53/116, 118, 281, 53/430, 471

[56] References Cited

U.S. PATENT DOCUMENTS

| | | |
|---|---|---|
| 2,620,028 | 12/1952 | Kohut . |
| 2,746,118 | 5/1956 | Drummond et al. . |
| 2,928,395 | 3/1960 | Forbes et al. . |
| 3,167,895 | 2/1965 | Egler et al. . |
| 3,611,551 | 10/1971 | Shave et al. . |
| 3,618,282 | 11/1971 | Hagel et al. . |
| 3,811,244 | 5/1974 | Killen et al. . |
| 3,816,889 | 6/1974 | Crotti . |
| 3,875,946 | 4/1975 | Duncan . |
| 3,980,177 | 9/1976 | McGregor . |
| 4,011,155 | 3/1977 | Feuerstein et al. . |
| 4,072,041 | 2/1978 | Hoffman et al. . |
| 4,255,917 | 3/1981 | Stone . |
| 4,424,898 | 1/1984 | Thyen et al. . |
| 4,651,879 | 3/1987 | Harris et al. . |
| 4,672,871 | 6/1987 | Gudmestad . |
| 4,722,384 | 2/1988 | Matsutani . |
| 4,744,035 | 5/1988 | Hashim . |
| 4,806,737 | 2/1989 | Coates . |
| 4,832,025 | 5/1989 | Coates . |
| 4,922,904 | 5/1990 | Uetake et al. . |
| 5,056,658 | 10/1991 | Sobel et al. . |
| 5,065,237 | 11/1991 | Tsikos et al. . |
| 5,150,307 | 9/1992 | McCourt et al. . |
| 5,226,336 | 7/1993 | Coates . |
| 5,230,424 | 7/1993 | Alpern et al. . |
| 5,253,765 | 10/1993 | Moorehead et al. . |
| 5,438,746 | 8/1995 | Demarest et al. . |
| 5,452,636 | 9/1995 | Rattan . |
| 5,469,689 | 11/1995 | Demarest et al. . |
| 5,473,810 | 12/1995 | Demarest et al. . |
| 5,473,854 | 12/1995 | Demarest et al. . |
| 5,477,609 | 12/1995 | Demarest et al. . |
| 5,485,668 | 1/1996 | Demarest et al. . |
| 5,487,212 | 1/1996 | Demarest et al. . |
| 5,487,216 | 1/1996 | Demarest et al. . |
| 5,491,954 | 2/1996 | Sobel ..................................... 53/281 X |
| 5,491,955 | 2/1996 | Sobel ..................................... 53/281 X |
| 5,500,991 | 3/1996 | Demarest et al. . |
| 5,511,670 | 4/1996 | Demarest et al. . |
| 5,660,024 | 8/1997 | Ivanov et al. ............................. 53/430 |
| 5,661,954 | 9/1997 | Ivanov et al. ............................. 53/430 |
| 5,664,404 | 9/1997 | Ivanov et al. ............................. 53/430 |
| 5,873,212 | 2/1999 | Esteves et al. ............................. 53/118 |

FOREIGN PATENT DOCUMENTS

| | | |
|---|---|---|
| 428253 | 5/1991 | European Pat. Off. . |
| 581699 | 2/1994 | European Pat. Off. . |
| 2632850 | 12/1989 | France . |
| 89 04 145 | 7/1989 | Germany . |
| 63-212027 | 9/1988 | Japan . |
| 63-299834 | 12/1988 | Japan . |
| 3-82458 | 4/1991 | Japan . |
| 3-106530 | 5/1991 | Japan . |

*Primary Examiner*—Daniel B. Moon

[57] ABSTRACT

A machine for the automated packaging of armed sutures or; in effect, surgical needles having sutures attached thereto and, more particularly, a suture capture and tensioning arrangement in an automated machine for the high-speed individualized packaging of single or individual surgical needles each having an attached suture into a tray and detachable cover providing a suture package utilized for the packaging of the individual or single needles and attached sutures.

19 Claims, 9 Drawing Sheets

SUTURE CAPTURE AND TENSIONING ARRANGEMENT IN A MACHINE FOR THE AUTOMATED PACKAGING OF NEEDLES AND ATTACHED SUTURES

BACKGROUND OF THE INVENTION

1. Field of the Invention

The present invention relates to a machine for the automated packaging of armed sutures or; in effect, surgical needles having sutures attached thereto and, more particularly, pertains to a suture capture and tensioning arrangement in an automated machine for the high-speed individualized packaging of single or individual surgical needles each having an attached suture into a tray and detachable cover providing a suture package utilized for the packaging of the individual or single needles and attached sutures. Additionally, the automated packaging machine incorporates operative mechanism adapted to wind the sutures into a peripheral channel of the tray and facilitating the attachment of the cover to the tray which contains the single needle and attached wound suture, and which cover concurrently constitutes a product-identifying label as a component of the tray. The cover being shaped such that removal of the cover is not necessary to enable a user to gain access to the contents of the tray; in essence, the armed suture.

The automated packaging machine also provides for a rotary turret or dial-like turntable for the high-speed loading thereof with empty trays; the sequential loading of successive forwardly indexed trays each with a needle and attached suture; the indexed advance of the needle and suture-filled tray to suture-winding stations of the machine during which interval the portions of the suture which extends outwardly of the tray in which the needle is packed is maintained under a predetermined controlled tension; the conveyance of the trays each containing the needle and attached wound suture to a cover-applying station of the machine to provide the completed suture packages, and the further advance of the suture packages for subsequent automated removal of the completed suture packages from the machine. The automated packaging machine is resultingly adapted to provide for the continuous and repetitive production of suture packages in a single high-speed production cycle without necessitating any manual manipulation thereof.

In order to facilitate the production of the suture packages as described herein, the present invention provides for a plurality of sequential operating stations, in which a first station includes carousel structure having stacked package trays sequentially conveyed to a rotary plate element which slices off or separates the bottommost package tray from a stack of trays, and includes operative robotic pivot arm structure for transferring the separated package tray to a tool nest mounted on a rotary dial for transfer to subsequent processing stations, where the package tray is provided with an armed suture, the suture wound into the package tray, a cover applied thereto to produce the finished package, and which is then removed from the packaging machine and further transported for additional processing and/or storage.

The present invention as disclosed herein is particularly directed to the provision of a novel arrangement and method for the automated capturing and tensioning of the sutures upon and subsequent to the introduction and transfer at a needle feed workstation of single surgical needles and portions of attached sutures into individual packaging trays until any remaining portions of the sutures which extend outwardly and downwardly from the trays mounting the surgical needles are wound into the trays in their entirety, so as to thereafter enable the application of covers thereto in sequential production steps through the intermediary of the automated packaging machine.

With respect to the foregoing, the capturing and tensioning of the suture portions extending outwardly and downwardly of the trays is implemented through the intermediary of novel vacuum clamp structure which is mounted on the turntable and operatively associated with each respective tool nest, and further controllable vacuum guide structure for guiding and tensioning the suture portions until these are wound into the confines of the packaging tray.

Currently, in the medical, surgical and health-related technology, the high-speed and efficient packaging of either single or multiple sutures which are each suitably attached to surgical needles, such as by being swaged or similarly fastened thereto, and in which such combined sets of needles and sutures are generally referred to as armed sutures, is imparted an increasing degree of importance in view of the rising demand of users for such combined surgical needles and attached sutures, and various diverse types of inexpensively manufactured suture packages for the containment of needles and attached sutures have been developed and are presently widely employed.

In specific instances, suture packages may be covered tray-shaped containers designed to receive and fixedly retain therein one or more needles and therewith attached sutures, in which the suture packages, upon opening of the covers, must enable the uncomplicated and simple withdrawal of a respective individual needle and its attached suture in a smooth unobstructed manner. In essence, when the needle which is to be removed from the suture package is engaged by a surgeon or health professional, for example, by being gripped through the intermediary of a forceps and then pulled out of the suture tray, it is essential that the needle easily disengage from its restraint in the package while the suture which is attached to the needle should also be readily able to slip out of the tray in the absence of any binding or snagging, and in the instance of the tray housing a plurality of armed sutures also without becoming entangled with other sutures still remaining in the suture tray or package. Thus, pursuant to a specific needle and suture package construction which, for example, may comprise an injection-molded plastic tray, the needles are generally engaged by clamping structure located in the tray so as to be "parked" or retained in predetermined position or array in a central region of the tray. The sutures extending from the needles to which they are attached, while being maintained captured under a controlled tension are then conducted into and deposited in a peripheral channel formed within the confines of the suture tray so as to extend along the peripheral length of the channel. This positioning of the needles, and particularly that of the sutures within the peripheral channel of the tray is intended to eliminate tight bends or curves normally imposed on the sutures so as to facilitate their easy withdrawal from the suture package.

2. Discussion of the Prior Art

Until relatively recently, the introduction of needles with attached sutures into suture packages or molded plastic trays was being implemented in a substantially manual manner. In that instance, the needles were manually placed into the tray so as to be clampingly engaged by means of suitable needle-gripping structure, and thereafter the attached sutures wound or positioned within the confines of the tray. Subsequently, a suitable cover was superimposed upon and fastened to the filled tray, and the resultant armed suture package conveyed to a suitable arrangement for possible sterilizing or further over wrapping.

The foregoing essentially manual and relatively basic process for winding the sutures into the tray, and especially the locating thereof into the peripheral channel of the tray during manipulation of the tray, was quite time-consuming, and in conjunction with the manual application of the cover into the tray in a basically individual or piece-by-piece mode, represented a serious hindrance to a large volume or mass produced manufacturing output, and adversely affected the economics in attempting to provide such large quantities of suture packages containing either single or multiple surgical needles and attached sutures.

As an improvement over the foregoing, there was then developed a generally semi-automated winder machine for packaging surgical needles and attached sutures in a tray-like suture package, and wherein at least some of the previously manually implemented packaging steps were to some extent automated in order to be able to increase the output of needle and suture-containing packages while simultaneously reducing the number of manual procedures in effectuating the packaging of those particular items.

To that effect, the semi-automated winder machine, although necessitating the manual orientation of the trays for implementing the filling thereof with needles and attached sutures, included a winding station which to a considerable degree automated the winding process for the sutures so as to place the latter into a peripheral channel extending about the circumference of the tray. Also provided was a further therewith operatively associated device which enabled covers to be manually placed on the needle and suture-filled trays to be fastened thereto by means of a pressing die forming latchingly engaging interconnections between each of the covers and the trays, while concurrently producing from a portion of the cover a product-identifying label which remains permanently attached to the tray upon subsequent detachment of the cover. Although providing a considerable advance over the state-of-the-art in the packaging of needles and sutures, the semi-automated winder machine nevertheless necessitated the implementation of a considerable number of manual and labor-intensive handling steps in effectuating the filling of the trays with surgical needles and attached sutures, attaching the cover and, generally, producing complete suture packages.

As a further technological advance over the foregoing semi-automated needle and suture package-forming concept, there was then developed a substantially fully automated packaging machine which is adapted, in a highly efficient and extremely rapid mode, to continually fill successive trays of the type described hereinabove with pluralities of surgical needles and attached sutures, and subsequently causing the sutures to be wound into the confines of the tray, such as into a peripheral channel extending about the tray. Thereafter, the packaging machine was designed to implement the automated positioning and fastening of covers to the needle and suture-filled trays to produce completed suture packages of the type described hereinabove, which were then adapted to be transported to a suitable locale for selective further processing, such as sterilizing, and/or over wrapping, as is required by this technology.

In particular, the automated packaging machine was designed to provide the packages with each housing a plurality of needles and attached sutures. For example, the packaging machine for accomplishing the foregoing, which is commonly assigned to the assignee of the present application, is described in U.S. Pat. Nos. 5,487,212; 5,473, 854; 5,469,689; 5,473,810; 5,511,670; 5,452,636; 5,438, 746; 5,500,991; 5,477,609; 5,485,668; and 5,487,216.

The flat, tray-shaped suture package produced by the packaging machine set forth in the above-mentioned patents provides for the storage therein of multiple surgical needles and attached sutures, while concurrently recognizing the need to facilitate the smooth and unobstructed withdrawal of individual needles and attached sutures from the suture package. For instance, such a suture package is disclosed in applicants U.S. Pat. No. 5,230,424, which is commonly assigned to the assignee of the present application; and wherein the suture package is referred to as an RSO package (Reduced Size Organizer).

In the specific design of the flat tray-shaped plastic container having a peripheral channel as disclosed in the above-mentioned patent, the suture package is basically constituted of a rectangular round-cornered and flat-bottomed injection-molded plastic tray having a flat central surface area including a raised needle clamping structure formed thereon for engaging and "parking" a plurality of needles in a predetermined spaced array. Sutures each have one end thereof attached to each of the respective needles so as to form so-called "armed sutures". The sutures extend from each of the needles into a channel extending about the perimeter or periphery of the suture tray and are conducted into the channel so as to be essentially wound within the circumferential confines of the suture tray. The plurality of sutures which are positioned within the suture tray channel are protected against inadvertent outward displacement therefrom through the presence of a multiplicity of contiguously positioned resilient fingers which are integrally molded with the suture tray, and which project outwardly above the confines of the channel along a major portion of the length of the channel and, collectively, form a so-called "zipper structure" in which the inherently resilient nature of the fingers facilitates their temporary raising up to enable the introduction of the sutures into the suture tray channel by means of a suitable suture winding apparatus.

Although the rotary dial or turntable apparatus of the packaging machine pursuant to the foregoing U.S. patents provides for the packaging of armed sutures; in effect, needles with attached sutures, in a rapid and fully automated manner, such as by supplying the tray-shaped packages; thereafter parking the plurality of armed sutures in the packages, applying covers and removing the completed suture packages from the machine in a sequential station-to-station procedure, the machine was designed to primarily produce suture packages each containing a plurality of armed sutures.

SUMMARY OF THE INVENTION

Pursuant to the present inventive concept, the above-mentioned automated packaging machine is further improved upon in a novel and unique manner in that the machine is adapted to produce suture packages each containing a single armed suture, such packages being frequently in demand rather than packages containing a plurality of needles and sutures. Thus, in order to provide for high production rates which are essentially compatible with those employed in the manufacture of suture packages each containing a plurality of armed sutures, the present invention contemplates the provision of a fully automated packaging machine with a considerably increased rate of operating speed and production capability so as to render the packaging machines economically viable in comparison with the previously described automated packaging machine, while maintaining structural and functional reliability and ease of construction and maintenance.

In order to attain the essentially automated packaging of singly-packaged or individual surgical needles with attached sutures, the automated packaging machine pursuant to the invention sets forth the provision of a rotary turret or dial-like turntable having a plurality of tool nests each possessing a suture tray supporting surface, with each tool next being circumferentially spaced about the turntable so as to be uniformly distributed about the periphery thereof. The rotary turret is rotated to cause the tool nests supporting packaging trays to be indexed forwardly so as to advance through a plurality of successive workstations which are adapted to, respectively, effectuate the supplying of each of the trays located on the tool nests or support surfaces with a single or individual surgical needle and attached suture, winding the suture into the confines of each needle and suture-containing tray, forming a latching engagement between a tray cover and the tray; and thereafter conveying each completed suture package to a station for removal from the machine and transfer to stacking bins or the like.

Operatively communicating in synchronism with the indexing rotation of the rotary turret is a carousel device housing stacks of trays, which is adapted to supply empty trays sliced or separated from the bottom of a respective stack of the trays to a rotatable platform, and includes operative robotic pivot arm structure to successively remove the trays from the rotatable platform and mount the empty trays on successive tool nests so as to be oriented in a vertical plane facing radially outwardly of the rotary turret. Thereafter, each tray is indexed sequentially forwardly by the rotary turret to a workstation which will impart movement to a portion of the tool nest having the tray supported thereon, whereby the tray remains oriented essentially vertically it is rotated angularly relative to the horizontal plane of rotation of the rotary turret. This movement enables a transfer device with a needle and suture swaying mechanism processing needle grippers at a further workstation to insert and position a surgical needle with its attached suture into a therewith aligned tray for retentive engagement with needle-engaging structure formed in the tray so as to grip and park the needle therein, with the suture extending from the needle and depending downwardly therefrom outwardly of the tray. The needle and suture-containing tray is then advanced forwardly on its respective tool nest to successive workstations responsive to indexed advance of the rotary turret wherein, at a first suture winding station, structure operatively cooperating with the tray and the tool nest supporting the tray imparts an initial rotational movement to the tray about an axis perpendicular to the plane of the while maintaining tray the depending suture under tension, and at a second subsequent winding station imparts a rapid winding motion to the tray over multiple predetermined rotations so as to fully wind the downwardly depending suture into a peripheral tray channel extending within the perimeter of the tray.

Thereafter, the tool nest mounting the tray with the needle parked therein and the attached suture which has been wound into the peripheral channel of the tray is advanced to a further workstation responsive to indexed rotation of the rotary turret; at which workstation an operating mechanism causes a bottommost cover to be sliced or separated from a stack of covers and transferred to a rotatable platform. The cover is then engaged by a robotically-controlled pivot arm which, under the action of a vacuum, pivots the cover into a vertical orientation and applies the cover onto the tray while concurrently imparting pressure to the cover to cause cooperating latching structure to clampingly fasten the cover to the needle and suture-containing tray. Upon completion of the cover-attaching sequence, the resulting completed suture package is indexed to a further workstation at which suitable grippers arm mechanism engages the suture package, and the suture package is disengaged from the tool nest on which it is supported and conveyed transferred to and stacked in repository or receiving unit to be readied for further processing, such as sterilizing, over wrapping or the like, as may be required.

The foregoing sequence of operative steps is continually repeated for each successive tool nest on the rotary turret or turntable sequentially receiving empty trays from the carousel, while preceding tool nests each mounting a tray are conveyed through the above-mentioned packaging cycle. Thus, a successive tray is always placed into a position of readiness at a following or subsequent workstation and processed in a similar manner as before described during the forward indexing motion of the rotary turret or turntable. This ensures a continuously repetitive packaging cycle for successive suture packages in a highly efficient and high-speed operation without the need for any manual intervention in the operation of the packaging machine.

Intermediate various of the workstations as set forth hereinbefore; there may be arranged other workstations incorporating sensors adapted to enable ascertaining the presence of empty trays at the initial workstation, for a verification of a needle having been inserted into the trays and for inspection of the trays subsequent to the winding of the sutures into the tray channels; checking for the application of the covers to the trays, and facilitating the possible ejection of incomplete trays or the removal from the machine of defective packages.

Accordingly, in order to facilitate the appropriate introduction of the suture into the interior space of the package tray, subsequent to or concurrently with the positioning the surgical needle and attached end of the suture in the tray and the transferring thereof, with a portion of the suture depending outwardly and downwardly therefrom, apparatus is provided to capture the depending portion of the suture and to impart controllable tension thereto, until such time as the suture is completely wound into a suture-receiving channel formed in the tray.

Respecting the foregoing, pursuant to the invention, in order to effectuate the capture and tensioning of the depending portion of the suture which extends outwardly and downwardly of the tray mounting the surgical needle to which the suture is attached, there is provided preferably an air or vacuum-controlled clamping arrangement for capturing the suture in which imparts a gripping action thereon. Upon the package tray with the surgical needle contained therein being advanced to further workstations along the indexed advance of the turntable or tool nest-mounting dial, such as utilized for winding the suture into the tray, the clamping arrangement releases the suture so as to enable the latter to be pulled upwardly towards the tray, but with tension and guidance being maintained on the suture by a plurality of vacuum nozzles and through a further device imparting a vacuum condition to the externally depending length of the suture. This will effectively tension the suture and enable the latter to be wound into the tray at subsequent suture winding workstations along the path of travel of the turntable.

It is, accordingly, an object of the present invention to provide an arrangement for capturing and controllably tensioning at least the portion of a suture extending from its attachment to the surgical needle and which depends outwardly and downwardly from the package tray containing the parked surgical needle prior to the winding of the suture into the tray.

Another object of the present invention to provide a vacuum-controlled arrangement for capturing and maintaining tension on the portion of the suture depending outwardly from the tray during advance of the package tray from the needle feed and transfer workstation towards subsequent winding workstations at which the suture is fully wound into the confines of the tray.

Still another object of the present invention is to provide a method of implementing the capture and controllable tensioning of the portions of a suture extending outwardly and downwardly from a package tray retaining a surgical needle and attached suture until the outwardly extending suture portion has been fully wound into the tray.

A further object is to provide a method for capturing and tensioning the outwardly projecting portion of a suture as described hereinabove by utilizing the inventive vacuum-generating suture capturing and tensioning arrangement.

BRIEF DESCRIPTION OF THE DRAWINGS

Reference may now be had to the following detailed description of a preferred embodiment of the automated packaging machine of the invention, taken in conjunction with the accompanying drawings; in which.

DETAILED DESCRIPTION OF THE PREFERRED EMBODIMENT

Figure 1:
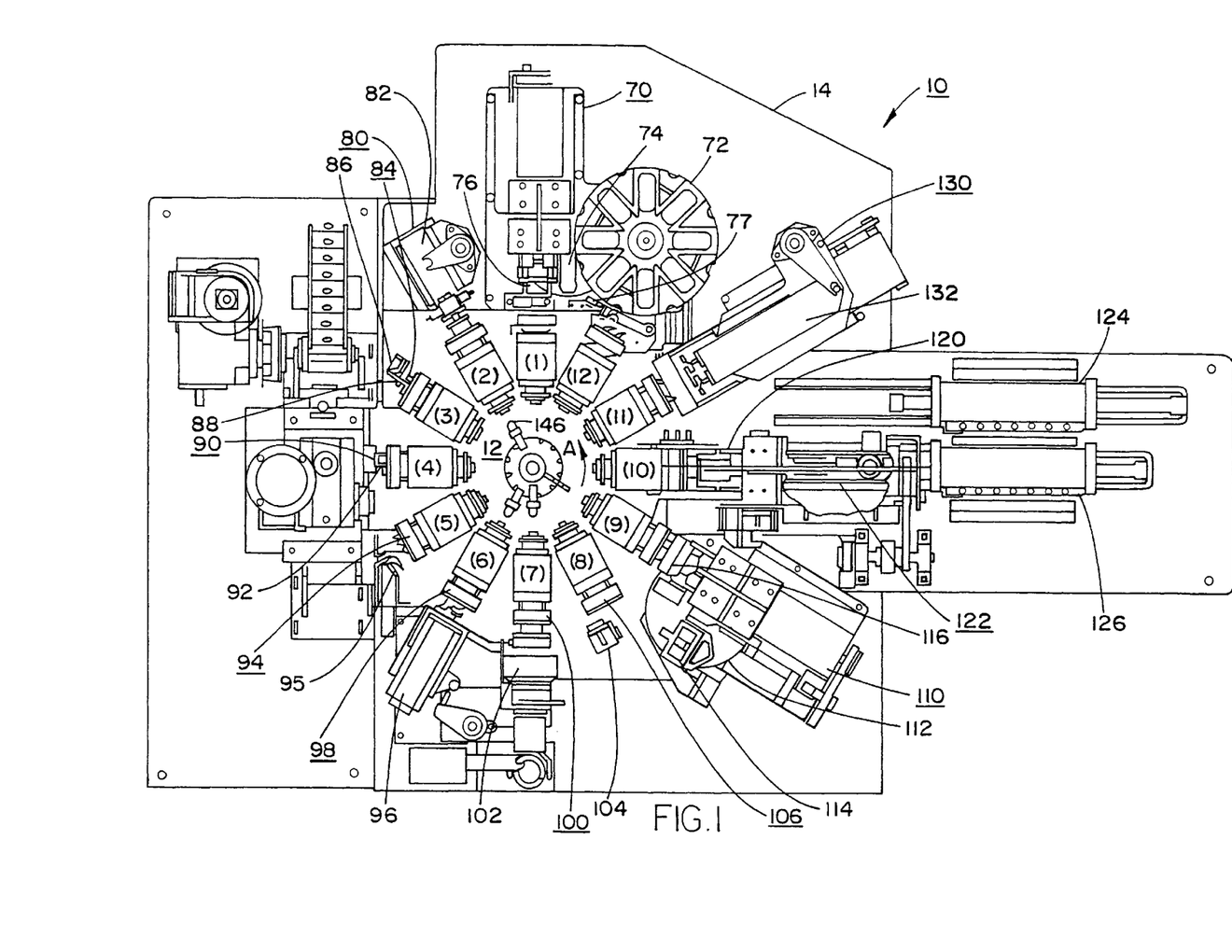
FIG. 1 illustrates, generally diagrammatically, a plan view of the machine for the automated packaging of individual surgical needles and attached sutures, pursuant to the present invention.
Figure 2:
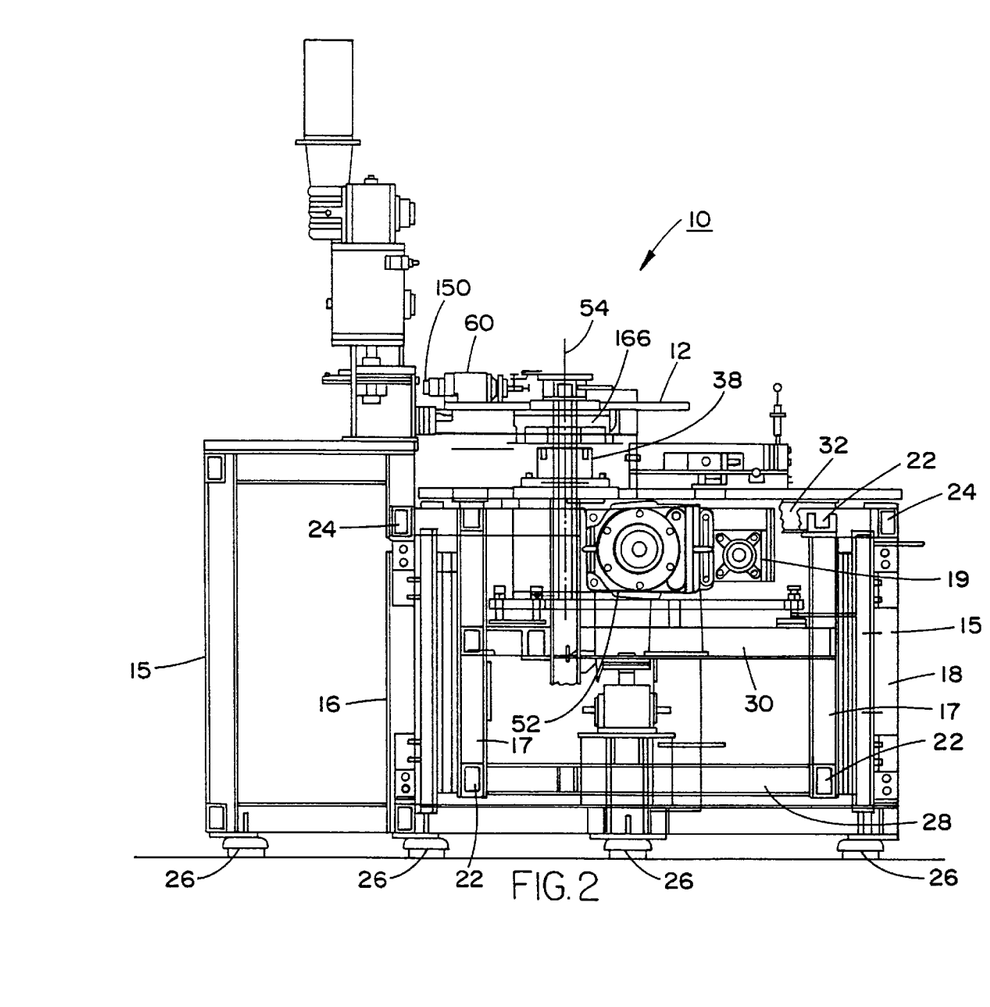
FIG. 2 illustrates a side elevational view of the frame structure for the machine of FIG. 1.
Figure 3:
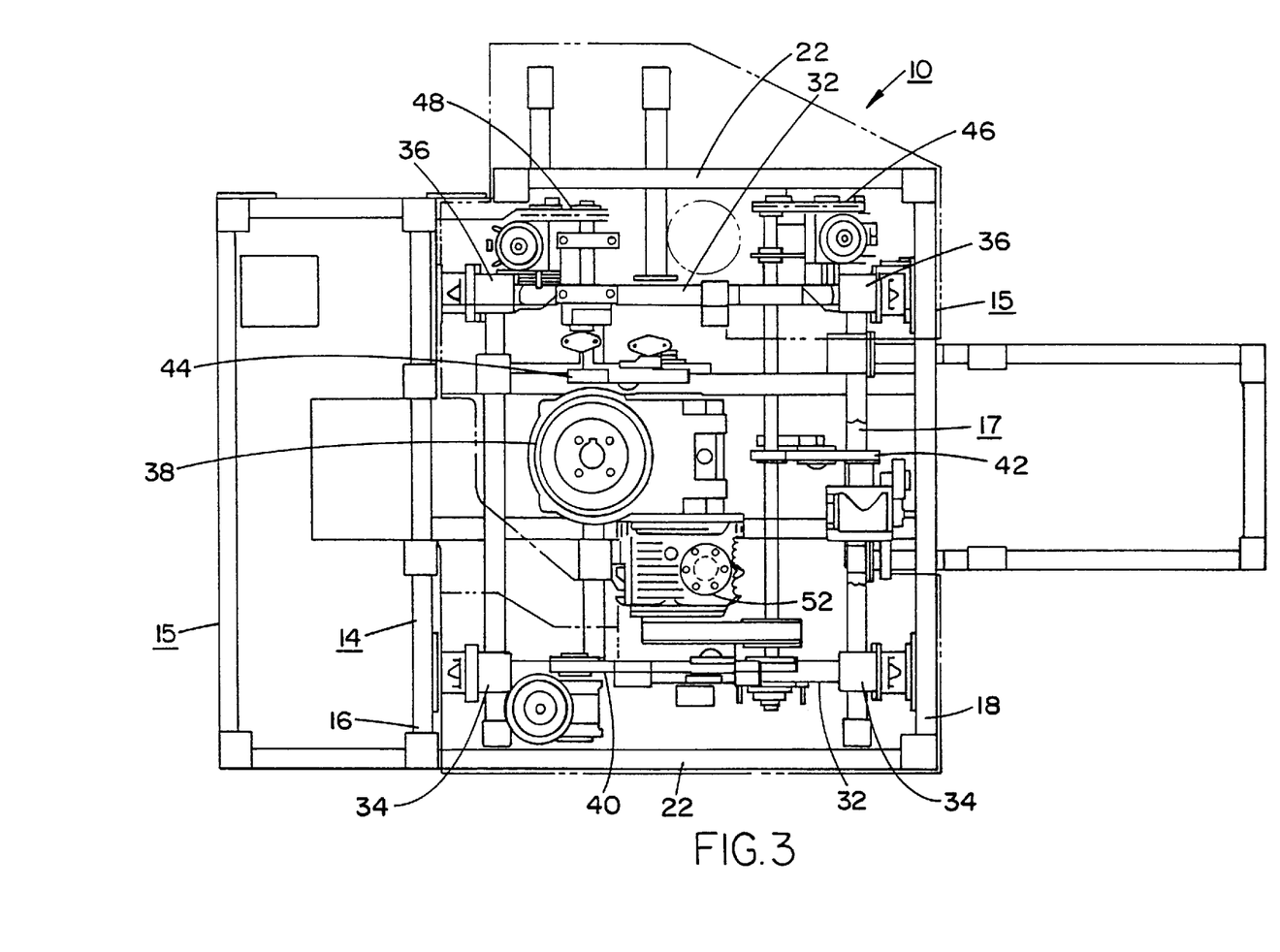
FIG. 3 illustrates a top plan view of the machine frame of FIG. 2.

Referring now in more specific detail to the drawings, FIGS. 1 to 3 illustrate, in a generally diagrammatic plan view, the automated needle and suture packaging machine 10 pursuant to the invention. The machine 10 comprises a rotary turret or turntable 12 which is essentially a packaging dial supported on an essentially stationary machine frame structure 14.

Figure 4:
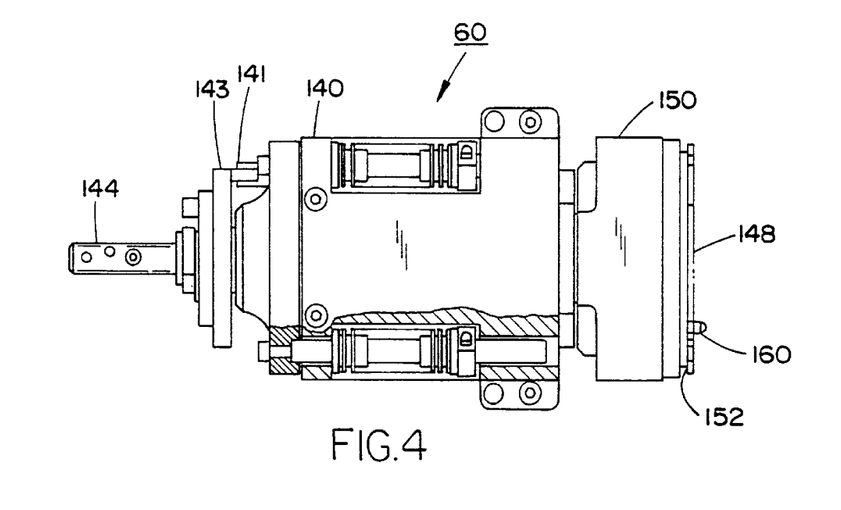
FIGS. 4, 5 and 6 illustrate, respectively, side, top plan and front end views of a tool nest utilized in the machine of FIG. 1.

The rigid frame structure 14, as illustrated in FIGS. 2 through 4, basically includes structural uprights 16 and 18, which are interconnected by horizontal beams 20, 22, 24, with the entire frame structure 14 adapted to be supported on a floor through the intermediary of adjustable leveling footings 26. The frame structure 14 comprises an outer stationary frame arrangement 15, and an inner vertically adjustable frame arrangement 17 comprising horizontal beams 28, 30 and 32, and vertical beams 34, 36 interconnected therewith supporting the turntable 12 for vertical adjustment relative to the stationary machine frame components. The vertical adjustment of the frame arrangement 17 is provided for by a central servo motor actuated jack screw 38, which also concurrently effectuates the vertical adjustment of all of the operative packaging devices at the various workstations of the machine so as to accommodate the packaging of a wide range of differently sized surgical needles without the necessity for modifying any machine components. Arranged within the frame structure are the various belt drives 40, 42, 44, 46 and 48 and operating drive components 50 for the machine, and the vacuum-generating systems 52 employed in the packaging cycles for the suture packages, as described hereinbelow. The turntable 12 is oriented in a horizontal plane, and through the intermediary of a program-controlled drive installation, is rotatable in an indexing or incrementally angular advance about a central vertical axis 54. In this instance, during operation of the machine, the turntable 12 is rotated in a counter-clockwise direction when viewed from above, as represented by arrow A, so as to be advanced in 30° increments.

The rotary turret or turntable 12 is essentially constituted of a circular disk-shaped member or packaging dial which has a plurality of tool nests 60 mounted thereon. The tool nests 60 are mounted in a circumferentially uniformly spaced array on the upper surface of the package dial or rotary turret 12, and with each tool nest 60 having an outer end projecting radially outwardly of the peripheral edge of the turret or dial 12, as described hereinbelow.

In this particular construction of the packaging machine 10, by way of example, twelve (12) tool nests 60 are arranged at uniformly distributed annular spacings of 30° from each other about the circumference of the dial or rotary turret 12.

In essence, as mentioned hereinbelow, the rotary turret or turntable 12 of the packaging machine 10 is adapted to be indexed forwardly in an angularly incremental or indexed rotational advance, each such incremental advance comprising one-twelfth of the 360° circumferential rotation of the turntable, or basically 30°, along the direction of rotation identified by arrow A in FIG. 1, such that the tool nests 60 which are each adapted to mount a suture tray or package are designed to be advanced in sequence to a number of successive workstations; designated herein as workstations (1) through (12), which are stationarily evenly spaced about the periphery of the rotary turret 12, as illustrated in FIG. 1 of the drawings.

The successive workstations which collectively constitute the automated machine 10 for the packaging of surgical needles and attached sutures are essentially briefly described as follows; viewed in the direction of rotation of arrow A:

(1) A first workstation 70 relates to the operative aspect of empty suture package trays being successively separated from the bottom of stacks of trays contained in a rotary carousel 72 to be transferred onto a rotationally indexed plate 74 under the action of a vacuum, and thereafter picked up and transferred by a cam-controlled robotic pivot arm structure 76 to successive tool nests 60 so as to be retained thereon while being conveyed by the rotary turret or dial 12 to subsequent workstations, as set forth hereinbelow.

(2) At this workstation 80, to which the respective tool nest 60 supporting the empty tray thereon has been advanced by the rotational advance of the turntable 12 mounting the tool nest; in effect, indexed 30° forwardly; operative slide-controlled pivot structure 82 engages a plate element on the outer end of the tool nest 60 which supports the empty tray under a vacuum, and rotates the plate element and tray counterclockwise within the vertical plane thereof about a horizontal radial axis of the tool nest 60 through an angle of approximately sixteen and one-half (16.5°) degrees so as to be in appropriate angular orientation relative to a horizontal axis for facilitating the subsequent insertion and retention of a surgical needle and attached suture into the tray.

(3) This workstation 84 provides for a sensor 86 which is mounted stationarily on a bracket arrangement 88 and faces the tool nest 60 so as to be able to check for the presence of an empty tray on the tool nest. The sensor 86 is suitably aimed at a black spot present on the packaging tooling nest, and in the absence of a tray being positioned thereon, enables deactivating the forward advance of the turntable 12 and concurrently may emit a signal to alert personnel regarding the missing tray.

(4) The next workstation 90 along the rotational path of motion of the turntable in the direction of arrow A, provides gripper mechanism 92 for inserting a single surgical needle and a therewith attached suture into the suture tray which has been indexed forwardly by the rotary turret 12 so as to be located in operative alignment with the needle-feed mechanism. The needles are conveyed by a mechanism so as to be mounted on suitable clamping or needle "park" structure constituting an integral portion of the tray. Vacuum-controlled suture capture and tensioning devices which are located below each tool nest 60, become operative at this workstation to capture and tension the suture portions depending outwardly and downwardly of the tray mounting the surgical needle.

(5) At this workstation 94, a stationary sensor 95 located radially outwardly of the turntable 12 may be utilized to ascertain the presence of a surgical needle and attached suture having been properly introduced into the tray at the previous workstation 90.

(6) A first tray winding mechanism 96 at this workstation 98 engages the plate element on the tool nest supporting the tray, while the suture capture and tensioning device ensures that the suture portion depending outwardly and downwardly from the tray is maintained under tension by a vacuum-operated tensioning device associated therewith, with the tray being rotated counterclockwise within its vertical plane through approximately 163.5°, to assume a horizontal orientation which is 180° inverse to its original orientation on the tool nest 60 at workstation (1), and with the remaining length of the suture being tensioned by the vacuum device externally of the tray.

(7) At a subsequent workstation 100, a further winding mechanism 102 engages the tool nest 60 and the tray mounted thereon, and imparts rapid rotation to the tray so as to enable tray structure engaging portions of the mechanism to introduce and completely wind the entire remaining length of the suture into a peripheral groove extending about the confines of the tray.

(8) A stationary sensor 104 at this workstation 106 is located radially outwardly of the turntable 12, and is adapted to ascertain the positioning of the surgical needle in the tray.

(9) This workstation 110 provides apparatus for the application and attachment of a cover or label to the tray containing the surgical needle and attached suture to produce or complete suture to produce a complete suture package. A rotatably indexed disc-like plate 112 includes a plurality of equidistantly circumferentially spaced cover-receiving areas, these being rotated below a vertical stack 114 of covers or labels such that, under the action of a vacuum, the bottommost covers of the stack are sequentially sliced off or separated and deposited into a respective area of the plate under the influence of the vacuum present therebeneath, and thereafter rotated into radial alignment with a tool nest 60 mounting the tray containing the surgical needle and attached wound suture. A cam-controlled robotic pivot arm structure 116 lifts the cover from the plate, while a subsequent area receives a further cover from the stack for transfer onto a following tray, and pivots upwardly and extends horizontally forwardly so as to position the cover into latching engagement with the tray, thereby forming the completed suture package.

(10) A robotic pivotable gripper arm 120 removes the completed package from the tool nest 60 at this subsequent workstation 122, and swings downwardly so as to deposit the completed suture package into receiving bins or compartments within elongated tray members 124 whereby upon a certain amount of trays being deposited to fill the tray member the latter is indexed to align a further empty compartment of a tray member with the tool nests. The tray member having the various filled compartments is then conveyed to a storage unit 126 and replaced automatically by another empty tray member.

(11) In the event of a suture package being defective, such as having a cover lacking or misplaced, and the resultant package has accordingly not been removed at the preceding package unloading workstation 122; at this workstation 130 a reciprocating arm structure 132 has a gripper head which engages and removes the rejected packages from the tool nests, and deposits them onto a conveyor belt 134 for conveyance to a suitable waste disposal site.

(12) A sensor 77 at the final workstation on the packaging machine 10 checks for the presence of a package that may not have been removed at stations (10) and (11). This is a further safeguard built into the packaging machine to ensure that the tool nest at station (1) is empty and ready to accept an empty package tray.

Figure 5:
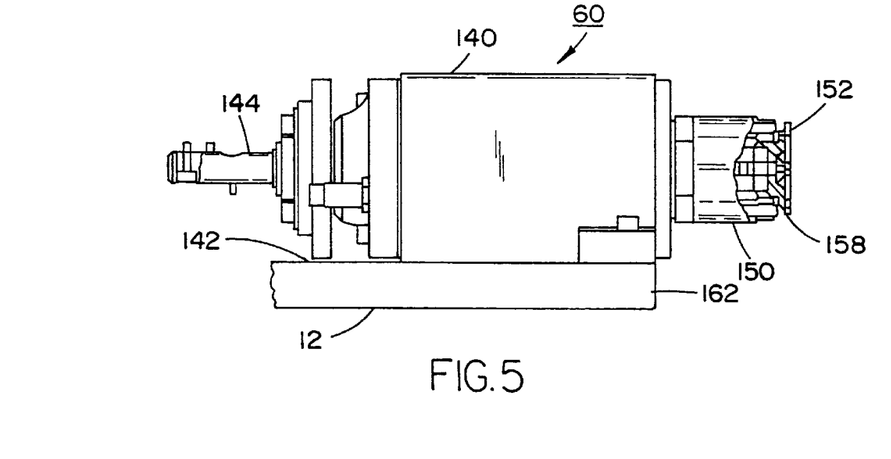
Figure 6:
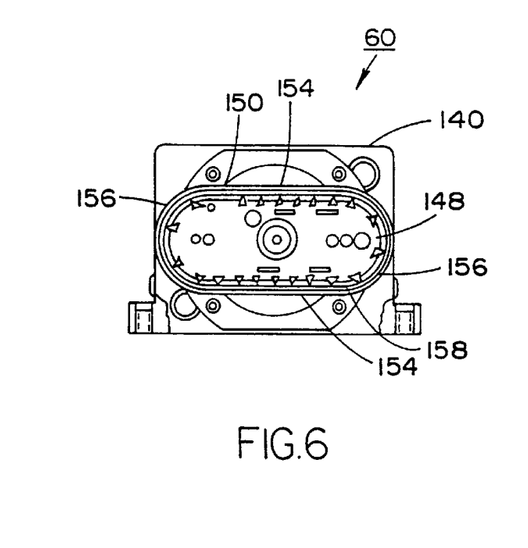

As shown in FIGS. 4 through 6, each tool nest 60 includes a housing 140 which is fixedly mounted on the upper surface 142 of the rotary turret 12. Each housing 142 includes a horizontal radially extending central through bore having a shaft 144 rotatably journaled therein. The shaft 144 is normally secured against rotation within housing 140; however, at predetermined workstations of the machine, the shaft 144 may be released by means of a locating pin 141 so as to be axially radially inwardly movable within housing 140 against stationary cam structure 143 mounted centrally on the rotary turret or dial 12 for regulating the rotational displacement which may be imparted to the shaft 144, as discussed hereinbelow in more specific detail.

The radially outwardly facing structure 148 of a plate element 150, which is fixedly secured to the radially outer end of shaft 144, is adapted for supporting suture package components, and particularly the package trays which are utilized in the production of surgical needle and attached suture-containing packages.

In essence, the radially outer structure of the tool nest housing 140 for mounting suture trays includes the plate element 150 which comprises an elongate vertically oriented plate member 152 having generally parallel opposite sides 154 and convexly rounded opposite ends 156 so as to be generally in conformance with the peripheral shape of a package tray. An external planar surface on the plate member 152 includes protruding perimeter or rim structure 158 for seating engagement therein of a suture tray, with the plate member 152 being fixedly secured to the radially outer end of the shaft 144 so as to be adapted for rotation therewith. Extending forwardly from the external planar surface of the rotatable plate member 152 of the tool nest 60 are protuberances or guide pins 160 which are intended to align the package tray thereon for appropriate positioning on the plate member 152, with the tray adapted to be retained thereon through the application of a vacuum to the exterior plate member surface through passageways communicating with a vacuum source connected thereto through the tool nest housing 140.

Figure 7:
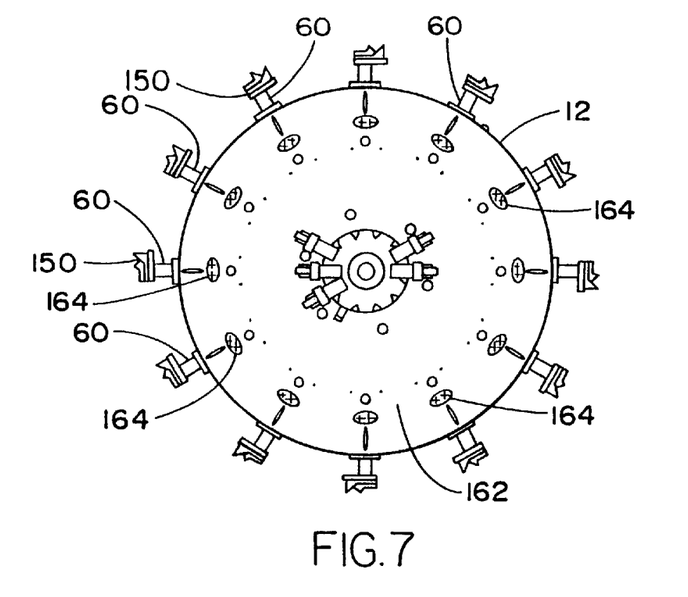
FIG. 7 illustrates a bottom view of the dial or turntable mounting the tool nests, showing vacuum ports for communicating with the tool nests and the vacuum clamp units for the sutures which extend outwardly of the package trays.
Figure 8:
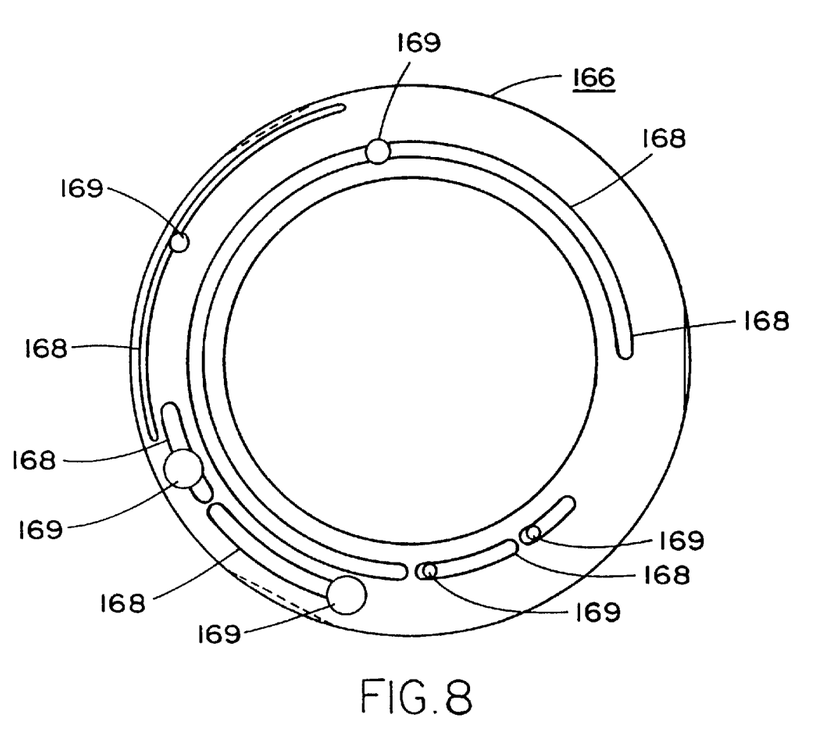
FIG. 8 illustrates a vacuum plenum for supplying the tool nests and vacuum clamp units with controlled vacuum conditions.

The vacuum passageways extend through the lower surface 162 of the dial or turntable 12, as shown in FIG. 7, which includes a plurality of apertures 164 each communicating with, respectively, passageways leading to an associated tool nest 60. The vacuum is supplied to the apertures 164 in a selective controlled mode through the intermediary of a stationary vacuum plenum 166 arranged below the dial 12, as shown in FIG. 2 of the drawings. The plenum 166, as shown in FIG. 8, includes outlet slots 168 and ports 169 for applying or closing a vacuum to respective tool nests 60 in accordance with the rotational positions of the dial 12 with the aperture or ports 164 in the lower surface 162 being in communication with the vacuum plenum outlet slots or ports.

With respect to the features of the packaging machine 10 which are directed to a provision of arrangements for capturing and tensioning the portion of the suture which depend outwardly of a packaging tray 170 during the cycle portion of machine operation in which the surgical needle and attached suture is transferred into and parked in a tray at needle feed or transfer workstation 90 (4) and until completion of the winding of the entire length of suture into the confines of the packaging tray, appropriate controlled tension must be maintained on the outwardly depending suture portion in order to avoid any snagging thereof which would inhibit or adversely affect the unobstructed winding of the suture into a channel formed in the tray 170.

Figure 9:
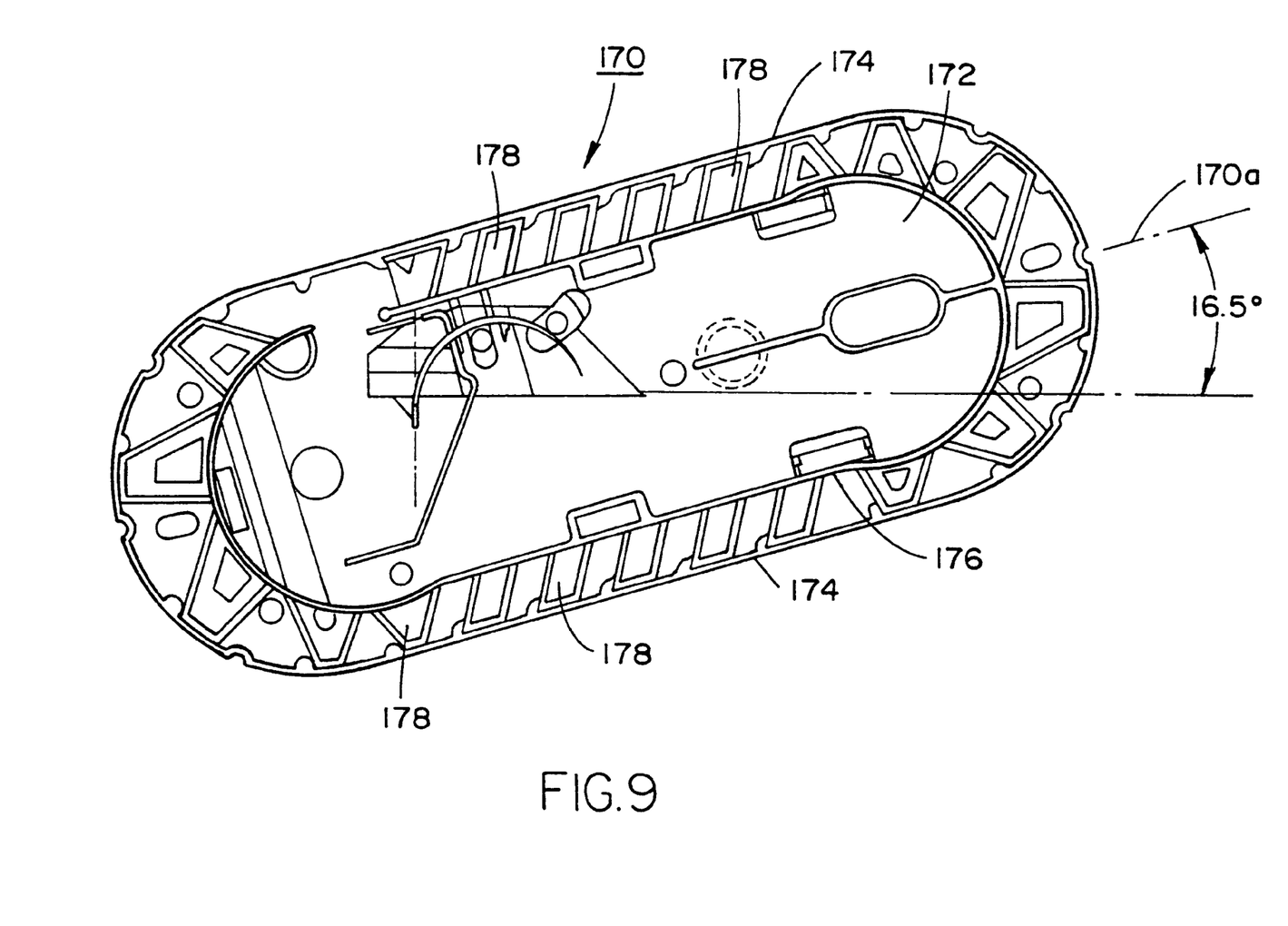
FIG. 9 illustrates a packaging tray having a surgical needle arranged therein upon the needle having been transferred thereto from a needle transfer mechanism.

The suture package tray 170, as shown in FIG. 9 of the drawings, is essentially constituted of molded plastic material, and includes a planar base 172 with parallel sides and semi-circular rounded ends. A vertical wall 174 extends about the perimeter of the tray, while inwardly spaced thereof is a second vertical wall 176 having radially outwardly extending fingers 178 which are flexible at the upper edge reaching close to the outer wall 174 so as to define a hollow channel structure. Apertures and surgical needle engaging structure is molded into the tray, as more specifically disclosed in copending U.S. Pat. application Ser. No. 08/521,978; filed Aug. 31, 1995 now U.S. Pat. No. 5,660,024, the disclosure of which is incorporated herein by reference, and which is commonly assigned to the assignee of this application.

As shown in FIG. 9 of the drawings, the packaging tray 170 is pivoted counterclockwise on the tool nest 60 to be at an angle of 16.5° relative to the horizontal, and remains at that angular orientation until the outwardly depending suture portion is begun to be wound into the packaging tray 170.

Figure 10:
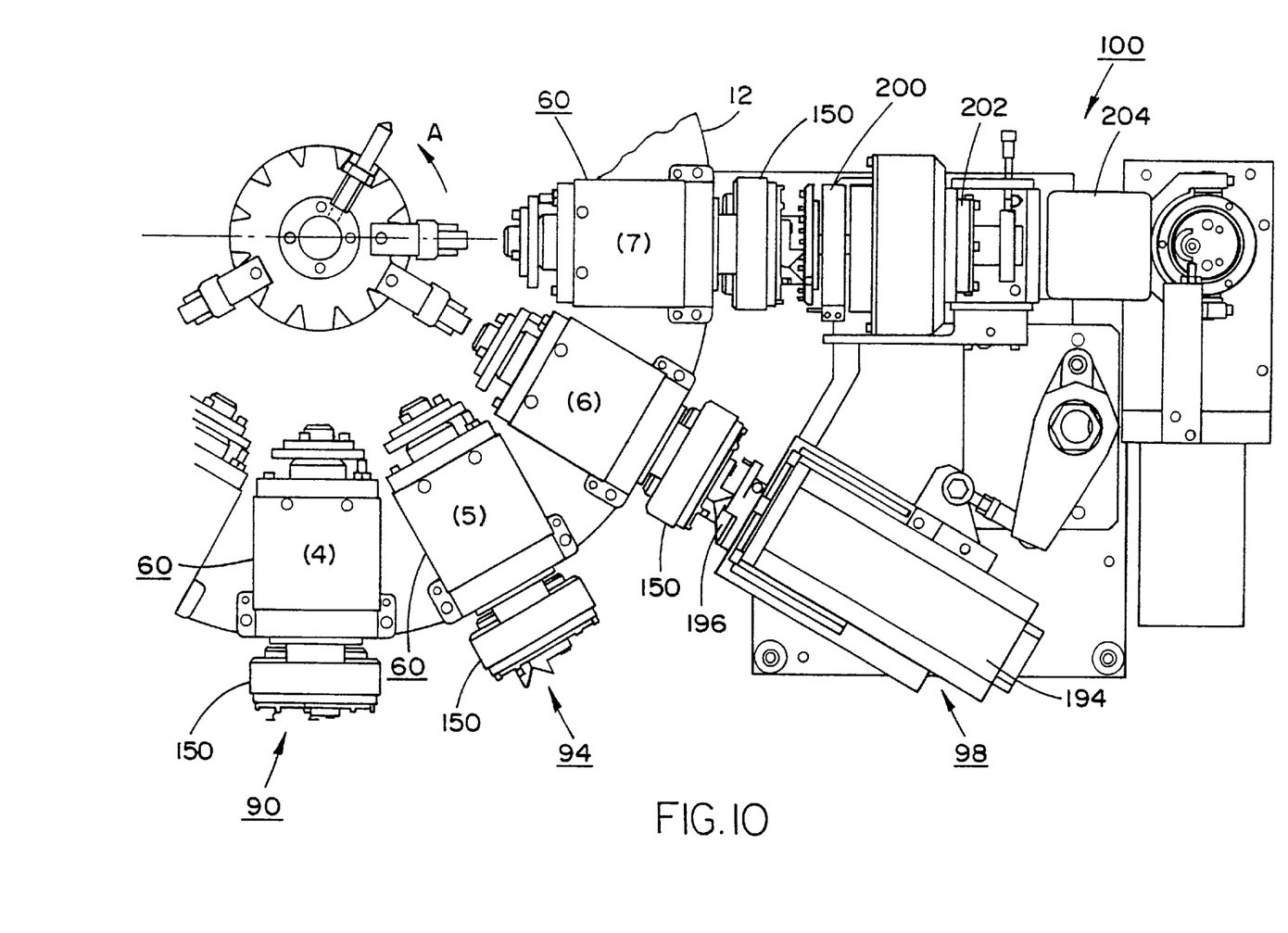
FIG. 10 illustrates a plan view of the workstations of the packaging machine at which the suture capturing and tensioning devices are in operative conditions.

Illustrated diagrammatically in FIG. 10 is a view of the workstations (4) through (7), between which there is effected the capture and tensioning of the suture portions extending outwardly from the packaging tray. At workstation (4), the surgical needle with attached suture has been transferred into the packaging tray 170 by the needle transfer apparatus disclosed in copending application Ser. No. 09/020,091 (Attorney Docket ETH-1191; 10196), the disclosure of which is incorporated herein by reference.

As the turntable 12 and the packaging trays 170 on the tool nest plate members 150 are advanced in the direction of arrow A, so that the tray 170 is indexed past the sensor workstation (5) at which it is inspected for the presence of a needle, and then indexed forwardly to winding stations (6) and (7), the suture capturing and tensioning system 190 is activated.

At the first winding workstation (6) a slide element 194 is reciprocated so that a winding head 196 causes a pin to engage the plate member 150 on tool nest 60. A drive (not shown) then rotates the plate member 150 together with the packaging tray 170 thereon counterclockwise through 163.5° so as to assume a horizontal orientation for the longitudinal tray axis. Thereafter, at the second winding workstation (7), a winding head 200 mounted on a rotatable winding unit 202 which is driven by a motor 204, causes the suture to be fully wound into the packaging tray 170. The winding stations (6) and (7) and the operative structures and detailed functions thereof are described in detail in copending application Ser. No. 09/020,191 (Attorney Docket ETH-1193; 10198), the disclosure of which is incorporated herein by reference.

Figure 11:
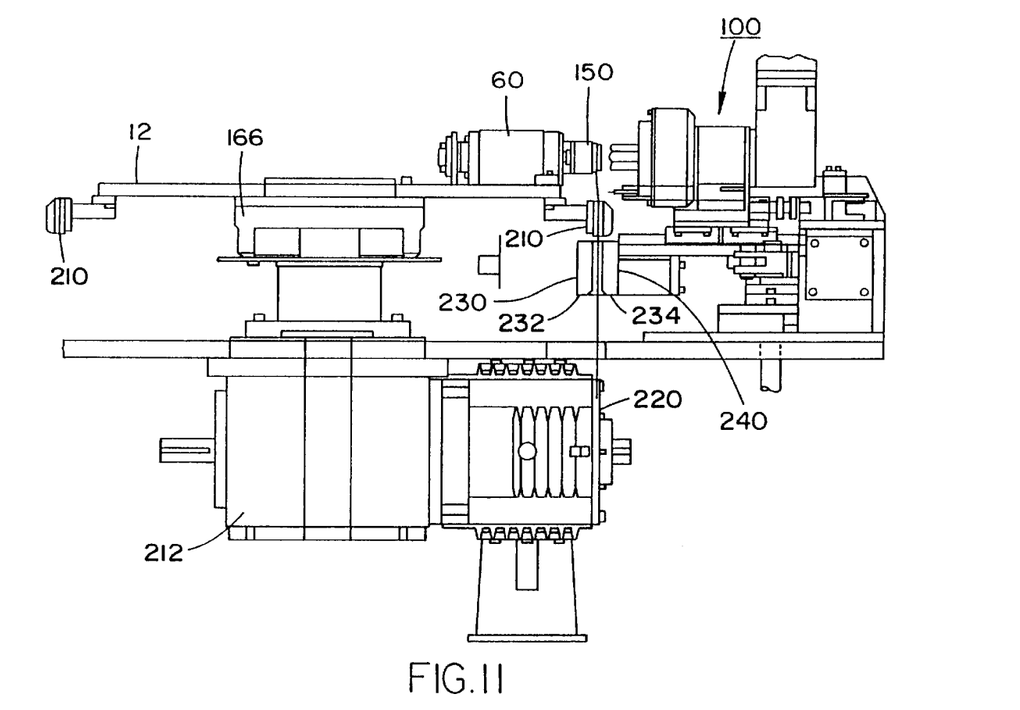
FIG. 11 illustrates an elevational view of the suture capturing and tensioning devices.
Figure 12:
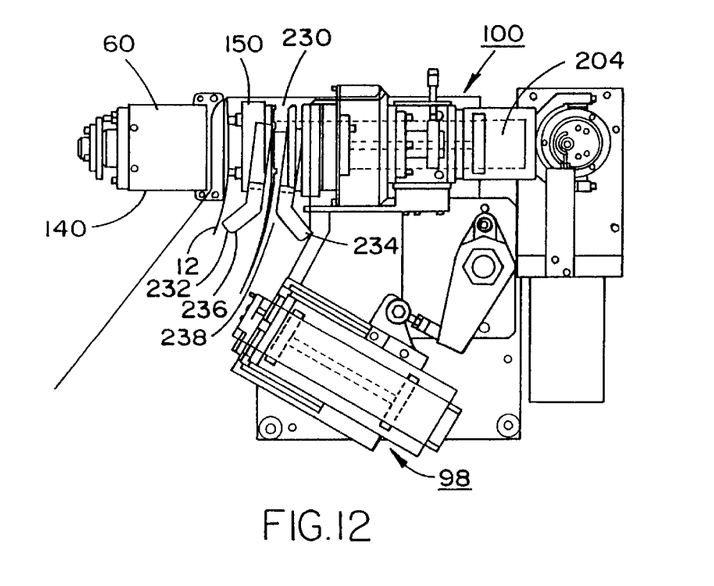
FIG. 12 illustrates a top plan view of suture winding arrangements.
Figure 13:
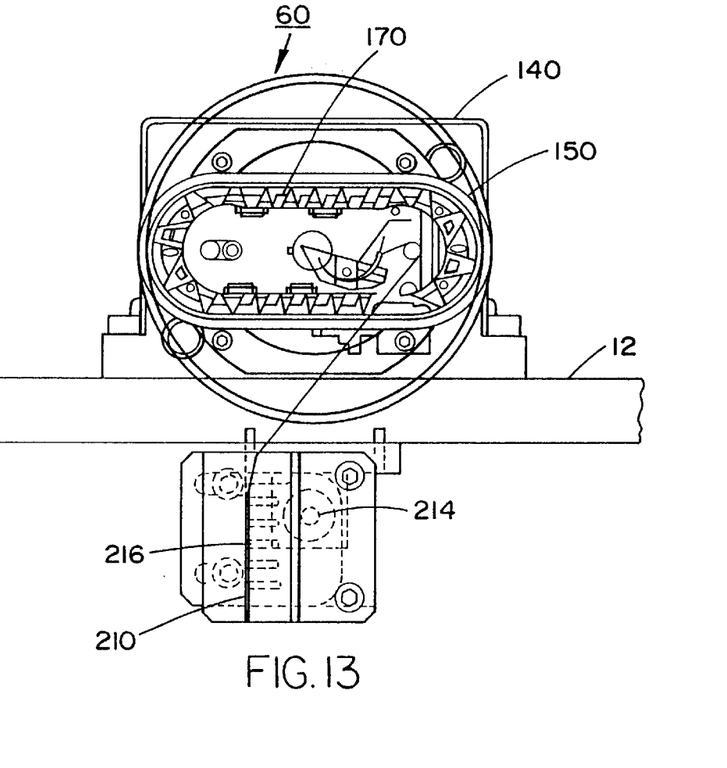
FIG. 13 illustrates a front view of the suture winding head of FIG. 11 with the suture clamp unit.
Figure 14:
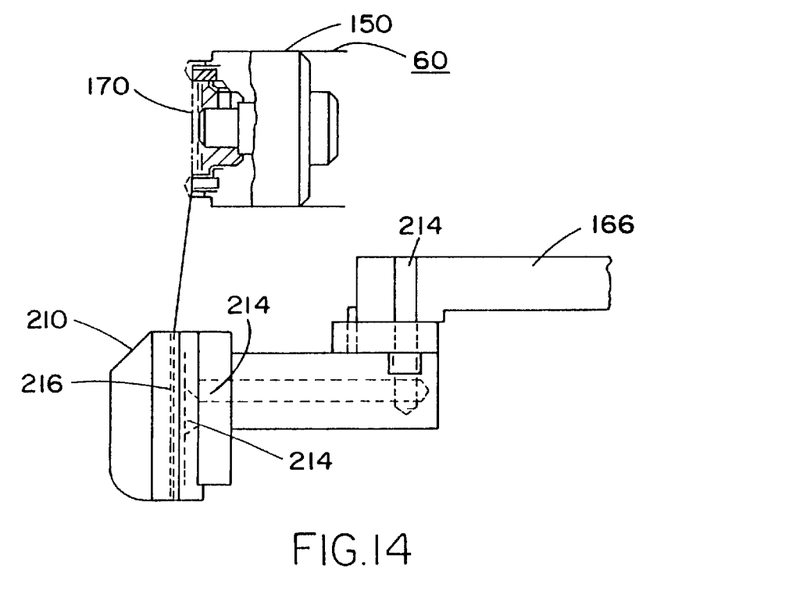
FIG. 14 illustrates a side view thereof.

Referring in particular to FIGS. 11 to 14 of the drawings, there is illustrated a vacuum-operated suture clamping unit 210, of which one each is mounted on the lower surface of turntable 12 beneath each respective tool nest 60 so as to extend below the plane of turntable 12. Each vacuum-operated suture clamping unit 210 is operative connected through the vacuum plenum 166 with a vacuum-generating system 212 provided in the packaging machine 10 and may be supplied with a controlled vacuum through suitable vacuum ports 214 and passageways as shown in FIG. 14 of the drawings, when a vacuum is intended to be supplied to sutures captured therein during predetermined operating intervals. In this instance, the clamping unit 210, which includes a plurality of vacuum nozzles or fingers 216 as illustrated in FIGS. 13 and 14, is rendered operative when a surgical needle is inserted into the packaging tray 170 at workstation (4), in effect, at the needle feed or transfer work station. The suture portion which extends outwardly and downwardly of the tray 170 from its end which is attached to the surgical needle which is is parked in the tray, is captured by the vacuum-operated clamping unit 210 through the intermediary of vacuum nozzles 216 at a location which is below the therewith associated tool nest 60.

When the surgical needle has been inserted into the tray 170 and the suture portion depends outwardly and downwardly therefrom, as illustrated in FIG. 11 of the drawings, it extends through the clamping unit 210, as shown in FIG. 11, and extends downwardly through a further vacuum nozzle arrangement 220 for tensioning the suture portion, and into a further lower suture tensioning device (not shown) which is also vacuum-operated and tensions the trailing end of the suture portion. Upon the tool nest 60 and the tray 170 with the surgical needle and attached suture having been advanced to the winding station (6) for initially rotating the tray 170 at winding station (6), shown in FIG. 13, and then advanced towards winding station (7) for winding the entire suture length into the confines of the tray 170, the vacuum in the nozzles 216 of clamping unit 210 is released, thereby permitting upward sliding movement therethrough of the outwardly extending suture portion towards the tray 170.

Moreover, as shown in FIGS. 11 and 12, a guide arrangement 230 for the depending suture portion is provided at winding workstation (7) below the clamping unit 210. The guide arrangement may comprises a pair of plates 232, 234 having wing portions 236 forming a conveying passageway 238 through which the suture is guided towards the winding head.

However, the suture is maintained under tension in that the vacuum is applied by the plurality of vacuum nozzles or fingers 240 which are located below the vacuum clamping unit 210. Consequently, although tension is maintained on the suture through the application of a vacuum, the suture is still permitted to move relative to the workstation at the surgical needle has been inserted into the tray, and at the workstations wherein the suture is adapted to be wound into the tray, as illustrated in copending application Ser. No. 09/020,191 (Attorney's Docket ETH-1193; 10198), the disclosure of which is incorporated herein by reference.

From the foregoing, it becomes readily apparent that the utilization of the vacuum-operated units 210 for capturing and the vacuum nozzle or finger devices for tensioning the suture portion which depends outwardly of the tray 170 when the latter has the surgical needle and attached suture end portion positioned therein, clearly facilitate the winding of the suture at subsequent workstations into the package tray while maintaining vacuum-generated control and tension on the suture, thus avoiding any snagging of the suture while being advanced and then wound into the tray.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A suture capture and tensioning arrangement in a machine for the automated packaging of a single needle having an attached suture to produce a suture package, wherein said machine automatically winds said suture within confines of a tray and attaches a cover to said tray so as to constitute said suture package, said machine having at least one tool nest for supporting said tray, and means for imparting a forwarding motion to said tool nest and said tray supported thereon for indexed advance to a plurality of workstations stationarily arranged proximate a path of advancing movement of said at least one tool nest; said arrangement comprising:

(a) suture clamping means located proximate said at least one tool nest, said suture clamping means being activated to clampingly engage a portion of a suture attached to a surgical needle retained in a tray mounted on said tool nest and depending therefrom at a workstation for feeding said needle to said tray;

(b) first vacuum-generating means for imparting a tension to said depending suture portion;

(c) and second vacuum-generating means for imparting tension to a trailing end of said depending suture portion.

2. An arrangement as claimed in claim 1, wherein said clamping means is activated at a workstation of said machine at which said surgical needle is transferred into said tray on a support surface of said tool nest so as to clampingly engage said depending suture portion, and is deactivated to release said suture portion upon said tool nest having advanced towards a subsequent winding workstation.

3. An arrangement as claimed in claim 1, wherein said first and second vacuum-generating means maintain tension on said depending suture portion during advance of said tool nest mounting said needle-containing tray towards a subsequent workstation.

4. An arrangement as claimed in claim 3, wherein said subsequent workstation comprises at least one further workstation for winding said depending suture portion into the confines of said tray.

5. An arrangement as claimed in claim 4, wherein said second vacuum-generating means continually imparts tension to the trailing end of said depending suture portion until the latter is wound into said tray.

6. An arrangement as claimed in claim 3, wherein said first and second vacuum-generating means are positioned proximate needle feeding and suture winding workstations of said machine.

7. An arrangement as claimed in claim 1, wherein said suture clamping means is fixedly connected with said at least one tool nest so as to be forwardly movable in conjunction therewith.

8. An arrangement as claimed in claim 1, wherein said clamping means is activated by a vacuum.

9. An arrangement as claimed in claim 1, wherein a plurality of said tool nests are mounted peripherally spaced about a rotatably indexed turntable, each said tool nest having respectively one said clamping means fixedly connected therewith.

10. An arrangement as claimed in claim 9, wherein each said clamping means is fastened to said turntable beneath a therewith associated tool nest.

11. A method of capturing and tensioning sutures in a machine for the automated packaging of a single needle having an attached suture to produce a suture package, wherein said machine automatically winds said suture within confines of a tray and attaches a cover to said tray so as to constitute said suture package, said machine having at least one tool nest for supporting said tray, and imparting a forwarding motion to said tool nest and said tray supported thereon for indexed advance to a plurality of workstations stationarily arranged proximate a path of advancing movement of said at least one tool nest; said method comprising:

(a) effecting suture clamping proximate said at least one tool nest, said suture clamping being activated to engage a portion of a suture attached to a surgical needle retained in a tray mounted on said tool nest and depending therefrom at a workstation for feeding said needle to said tray;

(b) through a first vacuum-generating device imparting a tension to said depending suture portion;

(c) and through a second vacuum-generating device imparting tension to a trailing end of said depending suture portion.

12. A method as claimed in claim 11, wherein said clamping is activated at a workstation of said machine at which said surgical needle is transferred into said tray on a support surface of said tool nest so as to clampingly engage said depending suture portion, and is deactivated to release said suture portion upon said tool nest having advanced towards a subsequent winding workstation.

13. A method as claimed in claim 11, wherein said first and second vacuum-generating devices maintain tension on said depending suture portion during advance of said tool nest mounting said needle-containing tray towards a subsequent workstation.

14. A method as claimed in claim 13, wherein said subsequent workstation comprises at least one further workstation for winding said depending suture portion into the confines of said tray.

15. A method as claimed in claim 14, wherein said second vacuum-generating device continually imparts tension to the trailing end of said depending suture portion until the latter is wound into said tray.

16. A method as claimed in claim 13, wherein said first and second vacuum-generating devices impart tension proximate needle feeding and suture winding workstations of said machine.

17. A method as claimed in claim 11, wherein said suture clamping is effected by means fixedly connected with said at least one tool nest so as to be forwardly movable in conjunction therewith.

18. A method as claimed in claim 11, wherein said clamping is activated by a vacuum.

19. A method as claimed in claim 11, wherein a plurality of said tool nests are mounted peripherally spaced about a rotatably indexed turntable.

* * * * *